United States Patent [19]

Bailey

[11] Patent Number: 4,705,047
[45] Date of Patent: Nov. 10, 1987

[54] OUTPUT CIRCUIT FOR PHYSIOLOGICAL MEASURING INSTRUMENTS

[75] Inventor: Wilber H. Bailey, San Diego, Calif.

[73] Assignee: Camino Laboratories, Inc., San Diego, Calif.

[21] Appl. No.: 782,080

[22] Filed: Sep. 30, 1985

[51] Int. Cl.$^4$ .............................................. A61B 5/02
[52] U.S. Cl. ................................... 128/672; 128/710
[58] Field of Search ............... 128/672, 693, 695, 723, 128/734, 735, 680, 681, 709, 710

[56] References Cited

U.S. PATENT DOCUMENTS

| | | | |
|---|---|---|---|
| 3,215,135 | 11/1965 | Franke ................................. | 73/705 |
| 3,267,932 | 8/1966 | Valliere ............................... | 128/675 |
| 3,400,709 | 9/1968 | Funfstuck ........................... | 128/672 |
| 3,585,988 | 6/1971 | Creigh ................................. | 128/709 |
| 3,971,365 | 7/1976 | Smith .................................. | 128/734 |
| 4,201,222 | 5/1980 | Haase .................................. | 128/634 |
| 4,223,681 | 9/1980 | Sherman ............................. | 128/672 |
| 4,242,730 | 12/1980 | Golias et al. ...................... | 364/416 |
| 4,325,382 | 4/1982 | Miodownik ........................ | 128/673 |
| 4,404,974 | 9/1983 | Titus ................................... | 128/670 |
| 4,417,306 | 11/1983 | Citron et al. ...................... | 364/415 |
| 4,487,206 | 12/1984 | Aagard ............................... | 128/667 |

Primary Examiner—Edward M. Coven
Assistant Examiner—J. P. Lacyk
Attorney, Agent, or Firm—Fulwider Patton Rieber Lee & Utecht

[57] ABSTRACT

An output circuit for a digital physiological measuring instrument. The output circuit provides means for a digital signal indicative of a physiological parameter to operate on an excitation signal from a monitor to provide a response signal for driving the monitor to generate a visual display of that parameter. The excitation signal is scaled in a digital-to-analog converter, corrected for a zero offset of the digital signal, and then applied to the monitor. A dummy excitation signal is provided to enable the output circuit to drive a readout device having an analog input but not providing an excitation signal.

12 Claims, 2 Drawing Figures

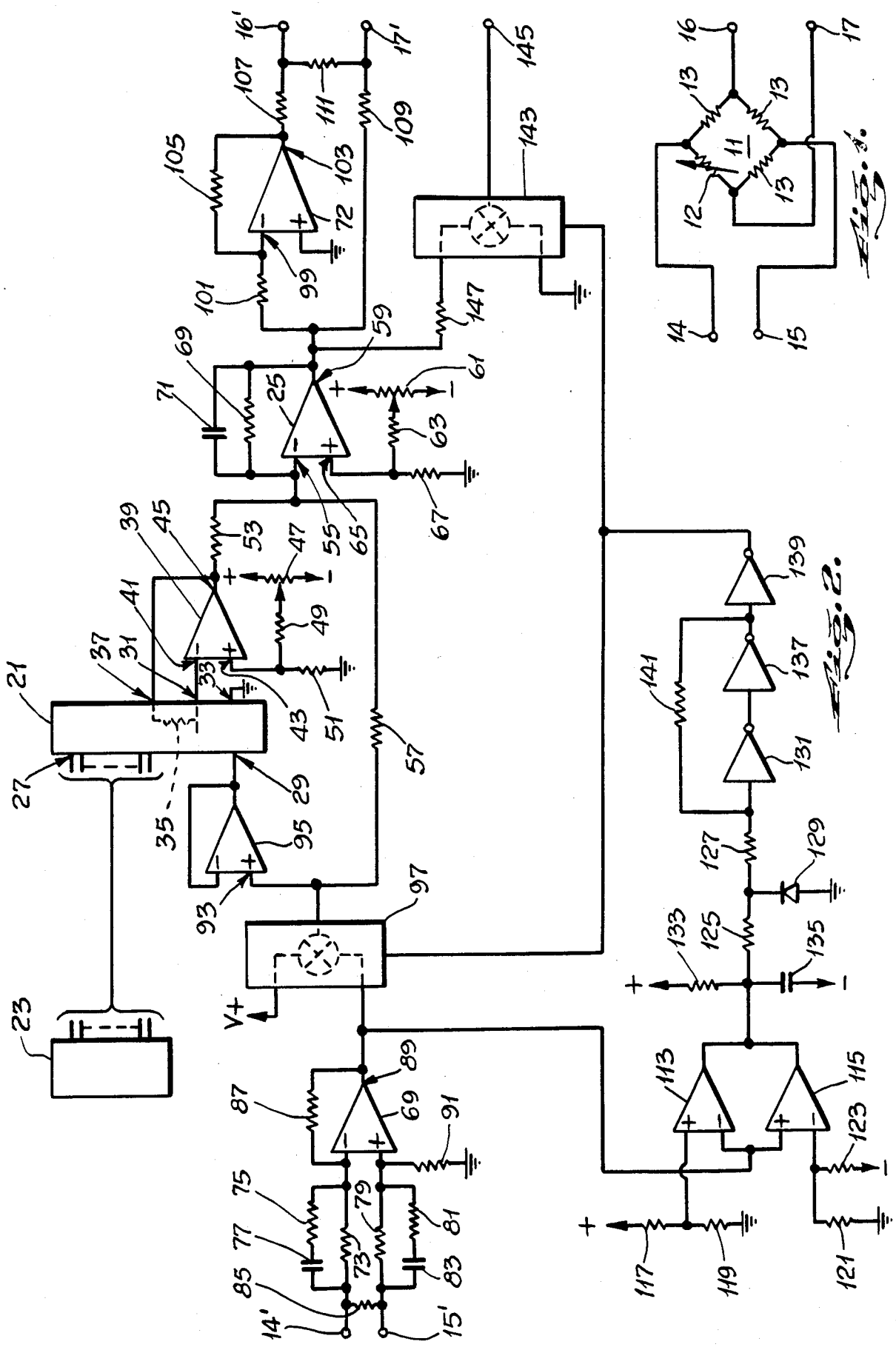

OUTPUT CIRCUIT FOR PHYSIOLOGICAL MEASURING INSTRUMENTS

BACKGROUND OF THE INVENTION

1. Field of the Invention

The present invention relates generally to instruments that measure physiological parameters and in particular to electronic instruments of the kind that generate digital signals indicative of physiological parameters to drive monitors that can generate visual displays representative of those parameters.

2. The Prior Art

Modern medicine employs electronic instruments to measure various physiological parameters such as body temperature or the pressure of various bodily fluids. One example of such an instrument is an electronic blood pressure meter for measuring blood pressure at a point within a human body. Such a blood pressure meter employs a transducer having a flexible member mechanically connected to one end of a catheter containing an inert fluid. The other end of the catheter is passed through a blood vessel in the body to the desired measurement point. Pressure exerted by the blood is transmitted through the inert fluid back to the flexible member, causing the flexible member to deform. As the flexible member deforms, a resistance strain gage, mechanically coupled to the flexible member, changes resistance in proportion to the magnitude of the pressure. The strain gage is wired as a leg of a Wheatstone bridge that can be electrically connected to an external blood pressure monitor for generating a visual display indicative of the blood pressure.

The external blood pressure monitor provides an excitation signal to the bridge and receives therefrom a response signal having a magnitude proportional to the blood pressure. Because the bridge is a simple resistance bridge, the excitation signal can have any desired magnitude up to several volts and any desired frequency from DC to several hundred kilohertz, and in practice excitation signals having various magnitudes and frequencies are provided by different blood pressure monitors on the market. A given monitor generates an accurate readout only if the bridge to which the monitor is connected has been excited by an excitation signal having the same magnitude and frequency as the excitation signal provided by that particular monitor.

Recent years have seen the development of digital electronic blood pressure meters having various desirable features not found in conventional electronic blood pressure meters of the kind described above. Such digital meters do not employ resistance strain gages and hence cannot be used with conventional external blood pressure monitors. Although it is possible to design new monitors to provide blood pressure readouts in response to digital output signals from such digital meters, presently there is no way a conventional monitor can generate a readout from such a signal. Conventional monitors are in widespread use in medical facilities, and it would be highly beneficial to be able to use these existing monitors in conjunction with the new digital blood pressure meters. Instruments that generate digital signals indicative of physiological parameters other than blood pressure are also finding increased use in the practice of medicine, and it would be advantageous to be able to use conventional monitors with these instruments as well as with the new digital blood pressure meters. Accordingly there is a need for a way to adapt a digital physiological measuring instrument to drive a conventional monitor to generate a visual display. The present invention satisfies this need.

SUMMARY OF THE INVENTION

The present invention provides an output circuit for a digital physiological measuring instrument, such as a blood pressure meter, to drive a conventional monitor to generate a visual display representative of the physiological parameter being measured The output circuit receives an excitation signal from the monitor. The excitation signal is scaled by a digital-to-analog converter to produce a scaled signal proportional to the value of a digital signal generated by the instrument. The scaled signal is shifted to compensate for a zero offset in the digital signal, as further described below, to generate a response signal for application to the monitor to generate the visual display.

The monitor generates a zero readout only if the response signal applied thereto is zero. However, the digital signal that indicates a physiological parameter having a value of zero is not itself zero, and hence, when the actual parameter is zero and the excitation signal is scaled by the corresponding digital signal, the result is a scaled signal having a non-zero value. The error in the visual display that would result if this scaled signal were applied directly to the monitor is constant over the entire range of the instrument, and therefore this error can be eliminated by subtracting from the scaled signal a constant signal equal to the value of the scaled signal that corresponds to a zero value of the parameter. Accordingly, a fraction of the excitation signal corresponding to the zero parameter value of the scaled signal is subtracted from the scaled signal in a summing amplifier to generate the response signal for application to the monitor.

Means are provided to detect the presence of an excitation signal and in the absence of such a signal to apply to the digital-to-analog converter a substitute excitation signal to enable the output circuit to provide a response signal to an auxiliary readout device, such as a strip chart recorder, that does not provide an excitation signal.

It will be appreciated from the foregoing that the present invention represents a significant advance in digital physiological measuring instruments. In particular, a digital blood pressure meter according to the present invention can drive a conventional blood pressure monitor to generate a visual display of the blood pressure regardless of the characteristics of the response signal required by that particular monitor, and an instrument that generates a digital signal indicative of some other physiological parameter can, in similar fashion, drive a similar monitor. Other aspects and advantages of the present invention will become apparent from the following more detailed description taken in conjunction with the accompanying drawings.

BRIEF DESCRIPTION OF THE DRAWINGS

FIG. 1 is a diagram of a prior art resistance bridge blood pressure meter for connection to a conventional blood pressure monitor; and FIG. 2 is a schematic diagram of an output circuit according to the present invention.

DESCRIPTION OF THE PREFERRED EMBODIMENT

Digital physiological measuring instruments that generate digital signals representing physiological parameters are not capable of driving conventional visual display monitors, but a digital physiological measuring instrument having an output circuit according to the present invention can drive such a monitor to generate a visual display indicative of the parameter being measured.

A conventional—as opposed to digital—electronic blood pressure meter, typical of physiological measuring instruments that can drive conventional monitors according to the prior art, includes a Wheatstone resistance bridge 11 having a leg 12 that changes resistance according to the blood pressure being measured and a plurality of other legs 13, as illustrated schematically in FIG. 1. An excitation signal, provided by a monitor (not shown), is applied to the bridge 11 through input terminals 14 and 15, and a response signal from the bridge appears at output terminals 16 and 17 for application to the monitor to generate a visual blood pressure display.

It will be apparent that a DC excitation signal applied to the terminals 14 and 15 results in a DC response signal at the terminals 16 and 17, and an AC excitation signal of a given frequency results in an AC response signal of the same frequency. It will also be apparent that the magnitude of the response signal is proportional to the degree of unbalance of the bridge, the constant of proportionality being determined by the magnitude of the excitation signal. Since the degree of unbalance of the bridge is proportional to the blood pressure being measured, the magnitude of the response signal is also proportional thereto, and the blood pressure monitor generates the display of the blood pressure by multiplying the response signal by the appropriate constant of proportionality as determined by the magnitude of the excitation signal.

An output circuit according to the present invention, as illustrated schematically in FIG. 2, has input terminals 14' and 15', corresponding to the input terminals 14 and 15 of the bridge 11, for receiving an excitation signal from a monitor, and output terminals 16' and 17', corresponding to the output terminals 16 and 17 of the bridge 11, for providing a response signal to the monitor. The output circuit comprises a digital-to-analog converter 21 for scaling the excitation signal, in proportion to a digital signal indicative of a physiological parameter such as blood pressure as provided by a digital instrument such as a blood pressure meter 23, to provide a scaled signal, and a summing amplifier 25 for applying a zero offset signal to the scaled signal to provide the response signal.

The converter 21 has a plurality of digital inputs 27 for receiving the digital signal from the digital blood pressure meter 23 and a reference input 29 for receiving the excitation signal. The converter 21 scales the magnitude of the excitation signal according to the value of the digital signal and provides the scaled signal at an output 31. A second output 33 is grounded, and an internal feedback resistor 35 provides a feedback path between the output 31 and a feedback terminal 37. In the preferred embodiment, a type DAC-1222 digital-to-analog converter is employed as the converter 21, although other types of digital-to-analog converters could be used.

The operation of the converter 21 is such that the magnitude of the scaled signal at the output 31 is proportional to the magnitude of the excitation signal applied to the input 29, and so long as the excitation signal is not equal to zero the scaled signal cannot be zero unless all of the bits of the digital signal applied to the inputs 27 are zero. However, the operation of the digital blood pressure meter 23 is such that a measured blood pressure of zero is represented by a digital signal having ones for some of its bits rather than zeros for all of its bits. It follows that an actual blood pressure of zero results in a scaled signal having a non-zero magnitude that is proportional to the magnitude of the excitation signal. If such a scaled signal were applied directly to a monitor, the resulting display would be erroneous because the monitor only gives a readout of zero if the applied signal is equal to zero. Hence, the scaled signal must be corrected to have a zero magnitude corresponding to an actual blood pressure of zero, and this correction is accomplished by the summing amplifier 25.

The scaled signal at the output 31 of the converter 21 is inverted by an inverting amplifier 39 having an inverting input 41, a non-inverting input 43, and an output 45, before it is applied to the summing amplifier 25. More particularly, the output 31 is connected to the inverting input 41, and an offset null correction signal, developed by a potentiometer 47 connected between a positive supply voltage and a negative supply voltage from a power supply (not shown), is applied from the variable contact of the potentiometer 47 through a resistor 49 to the non-inverting input 43. A resistor 51 provides a return to ground from the non-inverting input 43. The feedback terminal 37 of the converter 21 is connected to the output 45.

The inverted scaled signal appearing at the output 45 of the amplifier 39 is applied through a resistor 53 to a summing input 55 of the summing amplifier 25. The excitation signal is also applied to the summing input 55 through a resistor 57. The effect of summing the excitation signal with the inverted scaled signal is to subtract the one from the other to produce the response signal, appropriately shifted in magnitude to have a zero magnitude when the actual blood pressure is zero, at an output 59 of the summing amplifier 25. An offset null correction signal, developed by a potentiometer 61 connected between the positive supply voltage and the negative supply voltage, is applied from the variable contact of the potentiometer 61 through a resistor 63 to a non-inverting input 65 of the summing amplifier 25. A resistor 67 provides a return to ground from the non-inverting input 65. A feedback resistor 69 is connected in parallel with a filter capacitor 71 between the output 59 and the summing input 55, the capacitor 71 serving to filter out high frequency transients introduced into the scaled signal from the digital signal through the converter 21.

The blood pressure monitor provides a balanced excitation signal—that is, a signal carried by two leads isolated from ground—to the bridge 11 and receives therefrom a balanced response signal. However, the converter 21 operates on an unbalanced signal—that is, a signal carried by one lead with a return through a common ground. Accordingly, a differential amplifier 69 is provided to convert the balanced excitation signal as received from the monitor into an unbalanced signal for application to the converter 21, and a balancing amplifier 72 is also provided to convert the unbalanced response signal from the summing amplifier 25 into a balanced response signal for application to the monitor for generating the visual display.

The balanced excitation signal from the monitor is applied to the input terminals 14' and 15'. The terminal 14' is connected to an inverting input of the amplifier 69 through a first resistor 73 connected in parallel with a series combination of a second resistor 75 and a capacitor 77, and the terminal 15' is connected to a non-inverting input of the amplifier 69 through a similar network of resistors 79 and 81 and capacitor 83. A resistor 85 provides a dummy load for the excitation signal source. A feedback resistor 87 is connected between the inverting input and an output 89 of amplifier 69, and a return from the non-inverting input to ground is provided by a resistor 91.

The unbalanced excitation signal provided at the output 89 is applied to a non-inverting input 93 of an amplifier 95, and to the resistor 57, through a multiplexer 97. The amplifier 95 has an output connected back to its own inverting input to form a voltage follower for matching the input impedance of the converter 21 to the output impedance of the amplifier 69, and the output of the amplifier 95 is also connected to the input 29 of the converter 21.

The unbalanced response signal provided at the output 59 of the summing amplifier 25 is applied to an inverting input 99 of the balancing amplifier 72 through a resistor 101. The amplifier 72 has a non-inverting input connected to ground and an output 103 connected to the inverting input 99 through a feedback resistor 105 to provide an inverted image of the unbalanced response signal at the output 103. The inverted image of the response signal is applied through a resistor 107 to the output terminal 16', and the uninverted response signal from the output 59 is applied through a resistor 109 to the output terminal 17', to provide a balanced response signal. A resistor 111 is connected between the terminals 16' and 17' to provide a dummy source impedance to match the impedance of the response input of the monitor.

If no excitation signal is applied to the input terminals 14' and 15', no response signal will be generated. To provide a response signal for driving an auxiliary readout device, such as a strip chart recorder, that has an analog input but that does not provide an excitation signal, a dummy excitation signal V+, derived from the positive supply voltage, is applied to the converter 21 through the multiplexer 97 whenever a detecting circuit determines that an excitation signal is not present.

The output 89 of the amplifier 69 is connected to an inverting input of a first detecting amplifier 113 and to a non-inverting input of a second detecting amplifier 115. A non-inverting input of the amplifier 113 receives a positive bias from a junction between two resistors 117 and 119 connected between the positive supply voltage and ground, and an inverting input of the amplifier 115 receives a negative bias from a junction between two resistors 121 and 123 connected between the negative supply voltage and ground. Output signals from the amplifiers 113 and 115 are combined and applied through a first resistor 125 to a junction between a second resistor 127 and a cathode of a diode 129 that has its anode connected to ground, and from that junction through the resistor 127 to an input of a first digital inverter 131. A resistor 133 is connected between the outputs of the amplifiers 113 and 115 and the positive supply voltage, and a capacitor 135 is connected between the same outputs and the negative supply voltage. An output of the first inverter 131 is connected to an input of a second inverter 137 that has its output in turn connected to an input of a third inverter 139. The output of the inverter 137 is also connected through a resistor 141 back to the input of the inverter 131. The third inverter 139 drives the multiplexer 97 and a second multiplexer 143.

When an excitation signal is detected at the output 89 of the amplifier 69, the multiplexer 97 is activated to apply that signal to the voltage follower 95, and the multiplexer 143 is activated to short an auxiliary output 145 to ground. When the excitation signal is absent, both multiplexers are switched, the multiplexer 97 to apply the dummy signal V+ to the voltage follower 95 and the multiplexer 143 to apply the response signal from the output 59 of the summing amplifier 25 through the resistor 147 to the auxiliary output 145. In the preferred embodiment a first section of a type CD-4053B multiplexer having multiple sections is employed as the multiplexer 97 and a second section thereof is employed as the multiplexer 143, although other types of multiplexers could be used.

The filter capacitor 71, as described, filters high frequency transients out of the response signal However, it also tends to remove high frequency components that may have been present in the excitation signal. To counteract this tendency, the equalizer capacitors 77 and 83 and their associated components boost any high frequency components of the excitation signal enough to compensate for the effects of the capacitor 71.

An output circuit according to the present invention enables a physiological measuring instrument having only a digital output signal to operate on an excitation signal from a conventional monitor to create a response signal for driving that monitor to generate a visual display, thereby extending the usefulness of existing monitors by enabling them to be used with the latest digital physiological measuring instruments. Optionally, a strip chart recorder or the like having an analog input but not providing an excitation signal can also be driven directly by such a digital instrument.

Although one specific embodiment of this invention has been described and illustrated, it is to be understood that the invention is not to be limited to the specific forms or arrangements of parts so described and illustrated, and that various changes can be made within the scope of the invention. In addition, although a preferred embodiment has been disclosed in the context of a blood pressure meter, the invention also has applications in instruments that measure other physiological parameters. It is therefore to be understood that, within the scope of the appended claims, the invention may be practiced otherwise than as specifically described.

I claim:

1. In combination with a digital physiological measuring instrument for generating a digital signal indicative of a physiological parameter to drive a monitor, wherein the monitor provides an excitation signal having predetermined characteristics and is responsive to a response signal having similar characteristics to generate a visual display representative of the physiological parameter, an improved output circuit for accepting the excitation signal and generating the response signal, the output circuit comprising:
  scaling means responsive to the digital signal and to the excitation signal to generate a scaled signal having characteristics similar to those of the excitation signal and a magnitude proportional to the digital signal;

summing means responsive to the excitation signal and to the scaled signal to generate the response signal by subtracting from the scaled signal a portion of the excitation signal whereby the response signal is caused to assume a predetermined magnitude when the digital signal assumes a predetermined value;

means for applying the excitation signal to the scaling means; and means for applying the response signal to the monitor for generating the visual display.

2. An output circuit according to claim 1, adapted for driving an auxiliary readout device as well as the monitor, the output circuit also comprising:

detecting means for detecting the presence of an excitation signal; and means, responsive to the detecting means, for generating a response signal in the absence of an excitation signal by applying a substitute excitation signal to the scaling means when no excitation signal is present.

3. An output circuit according to claim 1, adapted to reduce high frequency transients introduced into the response signal by the scaling means, the output circuit also comprising:

filter means operative to reduce high frequency components of the response signal; and equalization means operative on the excitation signal to counteract the effect of the filter means on high frequency components introduced into the response signal by the excitation signal.

4. In combination with a digital physiological measuring instrument for generating a digital signal indicative of a physiological parameter to drive a monitor, wherein the monitor provides a balanced excitation signal having predetermined characteristics and is responsive to a balanced response signal having similar characteristics to generate a visual display representative of the physiological parameter, an improved output circuit for accepting the excitation signal and generating the response signal, the output circuit comprising:

a differential amplifier adapted to receive the balanced excitation signal and responsive thereto to generate an unbalanced excitation signal having characteristics similar to those of the balanced excitation signal;

a digital-to-analog converter, responsive to the digital signal and to the unbalanced excitation signal to generate a scaled signal having characteristics similar to those of the unbalanced excitation signal and a magnitude proportional to the digital signal;

a summing amplifier responsive to the unbalanced excitation signal and to the scaled signal to generate an unbalanced response signal by subtracting from the scaled signal a portion of the unbalanced excitation signal whereby the unbalanced response signal is caused to assume a predetermined magnitude when the digital signal assumes a predetermined value; and amplifier means adapted to receive the unbalanced response signal and responsive thereto to generate a balanced response signal for application to the monitor for generating the visual display.

5. An output circuit according to claim 4, adapted for driving an auxiliary readout device as well as the monitor, the output circuit also comprising:

detecting means for detecting the presence of an unbalanced excitation signal;

switching means, responsive to the detecting means, for generating a response signal in the absence of an excitation signal by applying a substitute excitation signal to the digital-to-analog converter when no excitation signal is present; and means for applying one of the response signals to the auxiliary device for generating a readout.

6. An output circuit according to claim 4, adapted to reduce high frequency transients that may be introduced into the scaled signal by the digital-to-analog converter, the output circuit also comprising:

a filter operative on one of the response signals to reduce high frequency components thereof; and equalization means operative on one of the excitation signals to counteract the effect of the filter on high frequency components introduced into the unbalanced response signal by the balanced excitation signal.

7. In an output circuit of a digital physiological measuring instrument operative to generate a digital signal indicative of a physiological parameter, an improvement whereby the instrument can drive a monitor that provides a balanced excitation signal having a predetermined frequency and is responsive to a balanced response signal to generate a visual display representative of the physiological parameter, the improvement comprising:

a differential amplifier adapted to receive the balanced excitation signal and responsive thereto to generate an unbalanced excitation signal having the same frequency as the balanced excitation signal;

a digital-to-analog converter, responsive to the digital signal and to the unbalanced excitation signal to generate a scaled signal of the same frequency as the unbalanced excitation signal and of a magnitude proportional to the digital signal and determined by the unbalanced excitation signal;

a summing amplifier responsive to the unbalanced excitation signal and to the scaled signal to generate an unbalanced response signal by subtracting from the scaled signal a portion of the unbalanced excitation signal whereby the unbalanced response signal is caused to assume a predetermined magnitude when the digital signal assumes a predetermined value; and amplifier means adapted to receive the unbalanced response signal and responsive thereto to generate a balanced response signal for application to the monitor for generating the visual display.

8. An improvement according to claim 7 whereby the instrument can drive an auxiliary readout device as well as the monitor, the improvement also comprising:

detecting means for detecting the presence of an unbalanced excitation signal;

switching means, responsive to the detecting means, for generating a response signal in the absence of an excitation signal by applying a substitute excitation signal to the digital-to-analog converter when no excitation signal is present; and means for applying one of the response signals to the auxiliary device for generating a readout.

9. An improvement according to claim 8, adapted to reduce high frequency transients that may be introduced into the scaled signal by the digital-to-analog converter, the improvement also comprising:

a filter operative on one of the response signals to reduce high frequency components thereof; and equalization means operative on one of the excitation signals to counteract the effect of the filter on high frequency components introduced into the unbalanced response signal by the balanced excitation signal.

10. In combination with a digital blood pressure meter for generating a digital blood pressure signal to drive a blood pressure monitor, wherein the monitor provides a balanced excitation signal having predetermined characteristics and is responsive to a balanced response signal having similar characteristics to generate a visual blood pressure readout, an improved output circuit for accepting the excitation signal and generating the response signal, the output circuit comprising:

a differential amplifier adapted to receive the balanced excitation signal and responsive thereto to generate an unbalanced excitation signal having characteristics similar to those of the balanced excitation signal;

a digital-to-analog converter, responsive to the digital signal and to the unbalanced excitation signal to generate a scaled signal having characteristics similar to those of the unbalanced excitation signal and a magnitude proportional to the digital signal;

a summing amplifier responsive to the unbalanced excitation signal and to the scaled signal to generate an unbalanced response signal by subtracting from the scaled signal a portion of the unbalanced excitation signal whereby the unbalanced response signal is caused to assume a predetermined magnitude when the digital signal assumes a predetermined value; and amplifier means adapted to receive the unbalanced response signal and responsive thereto to generate a balanced response signal for application to the monitor for generating the visual blood pressure readout.

11. An output circuit according to claim 10, adapted for driving an auxiliary blood pressure readout device as well as the monitor, the output circuit also comprising:

detecting means for detecting the presence of an unbalanced excitation signal;

switching means, responsive to the detecting means, for generating a response signal in the absence of an excitation signal by applying a substitute excitation signal to the digital-to-analog converter when no excitation signal is present; and means for applying one of the response signals to the auxiliary device for generating a blood pressure readout.

12. An output circuit according to claim 10, adapted to reduce high frequency transients that may be introduced into the scaled signal by the digital-to-analog converter, the output circuit also comprising:

a filter operative on one of the response signals to reduce high frequency components thereof; and equalization means operative on one of the excitation signals to counteract the effect of the filter on high frequency components introduced into the unbalanced response signal by the balanced excitation signal.

* * * * *